United States Patent [19]

Greiner et al.

[11] Patent Number: 5,310,858
[45] Date of Patent: May 10, 1994

[54] PROCESS FOR PREPARING POLYMERS OF P-XYLYLENE FROM P-XYLYLENE DIESTERS

[75] Inventors: Andreas Greiner; Peter Simon, both of Marburg, Fed. Rep. of Germany

[73] Assignee: Hoechst Aktiengesellschaft, Frankfurt am Main, Fed. Rep. of Germany

[21] Appl. No.: 10,431

[22] Filed: Jan. 28, 1993

[30] Foreign Application Priority Data

Jan. 31, 1992 [DE] Fed. Rep. of Germany ....... 4202672

[51] Int. Cl.$^5$ ............................................. C08G 61/04
[52] U.S. Cl. .................................... 528/271; 526/318; 528/373; 528/396; 528/422
[58] Field of Search ................ 528/271, 373, 396, 422; 526/318

[56] References Cited

U.S. PATENT DOCUMENTS

| | | |
|---|---|---|
| 3,149,175 | 9/1964 | Pollart . |
| 3,288,728 | 11/1966 | Gorham . |
| 3,300,322 | 1/1967 | De Geer . |
| 3,300,332 | 1/1967 | Gorham et al. ...................... 117/100 |
| 3,342,754 | 9/1967 | Gorham ................................ 260/2 |
| 3,412,167 | 11/1968 | Lewis . |

FOREIGN PATENT DOCUMENTS

| | | |
|---|---|---|
| 0294651 | 5/1988 | European Pat. Off. . |
| 650947 | 3/1951 | United Kingdom . |
| 673651 | 6/1952 | United Kingdom . |
| 807196 | 1/1959 | United Kingdom . |

OTHER PUBLICATIONS

*Encyclopedia of Polymer Science and Technology,* vol. 15, pp. 98–124 (Jun. 1972).
Chemical Abstract, vol. 118, No. 12, "New synthetic approach to film forming poly(p-xylylene)", Mar. 22, 1993.
Encyclopedia of Polymer Science and Technology vol. 15, (Plastics, Resins, Rubbers, Fibers), pp. 98 to 124, Jun. 1971.

*Primary Examiner*—Harold D. Anderson
*Attorney, Agent, or Firm*—Curtis, Morris & Safford

[57] ABSTRACT

The invention relates to a process for preparing compounds of the formula (I)

$$\text{—(CH}_2\text{—Ar—CH}_2\text{)}_{\overline{n}} \quad \text{(I)}$$

by pyrolysis, where n is the degree of polymerization and is $\geq 2$.

For this purposes compounds of the formula (II)

$$\text{—R—CO—O—CH}_2\text{—Ar—CH}_2\text{—O—CO—R} \quad \text{(II)}$$

are pyrolyzed in one stage under conditions resulting in cleavage of the ester bonds under a partial pressure of the esters of $p \leq 10$ mbar at temperatures $T \geq 500°$ C., with the formation of the corresponding derivatives of 1,4-dimethylene-2,5-cyclohexadiene, but without the latter being cleaved further in subsequent reactions. The polymers of p-xylylene formed by spontaneous polycondensation of the derivatives of 1,4-dimethylene-2,5-cyclohexadiene were then cooled, Ar and R have the following meanings:

—Ar— is a 1,4-phenylene radical or another C$_6$-C$_{12}$ aromatic or heteroaromatic radical in which the bonds are in the para position or a comparable coaxial or antiparallel position;

R— is preferably branched or unbranched C$_1$-C$_4$-alkyl or C$_6$-C$_{12}$-aryl radical.

7 Claims, No Drawings

PROCESS FOR PREPARING POLYMERS OF P-XYLYLENE FROM P-XYLYLENE DIESTERS

Poly-p-xylylene is a material with unusual chemical and physical properties. It is a crystalline polymer that is not attacked at room temperature by any known organic solvents. Its melting point and decomposition temperature are 420° C. Poly-p-xylylene is prepared in some industrially employed production processes (Encyclopedia of Polym. Sci. Tech. 15, 98, New York 1971) by spontaneous polymerization of 1,4-dimethylene-2,5-cyclohexadiene, which is condensed from the vapor phase on a surface thermostatically controlled below a certain critical temperature. Poly-p-xylylene is therefore particularly suitable as a chemically, thermally and mechanically stable coating. Typical applications are coatings of microelectronic components to exclude moisture and dirt, dielectrics in high packing density capacitors, particle encapsulation and gas barrier layers (Encyclopedia of Polym. Sci. Tech. 15, 98, New York 1971).

The preparation of poly-p-xylylene according to the prior art takes place in two successive pyrolysis stages from p-xylene. In the first stage p-xylene is pyrolyzed with the addition of steam, methane or nitrogen at 950° C to form tricyclo(8,2,2,2,4,7)hexadeca-4,6,10,12,13,15-hexaene (paracyclophane) (U.S. Pat. No. 3,149,175, U.S. Pat. No. 3,412,167). In the subsequent, second stage paracyclophane is cleaved to form 1,4-dimethylene-2,5-cyclohexadiene(quinodimethane), which is then condensed below a critical temperature on a surface, where it spontaneously polymerizes. This pyrolysis is carried out at temperatures from 550 to 700° C. and at pressures of $\leq 1.5$ mbar (U.S. Pat. No. 3,342,754, U.S. Pat. No. 3,288,728, U.S. Pat. No. 3,300,322). The disadvantage of the process is in particular the fact that two pyrolysis stages are required. Paracyclophane, which should actually be regarded as the monomer building block, can be prepared only with great effort and expense and in moderate yields. Alternative methods of preparing paracyclophane (EP-A-294 851) or the polymer (GB-A-807 196) via a Hoffmann elimination not provide any advantages for industrial processes on account of the high salt content obtained.

A further disadvantage is the fact that substituted poly-p-xylylenes cannot be obtained by using commercially available substituted p-xylenes. The substituents must instead be introduced by preparative organic chemistry methods at the paracyclophane stage (U.S. Pat. No. 3,288,728). Alternative methods of preparing substituted paracyclophanes involve considerable preparative complexity.

Attempts to prepare poly-p-xylylene by direct one-stage pyrolysis of xylene at up to 1000° C. have not been very successful, and resulted in poorly definable, cross-linked polymers having a marked coloration (GB-A-650 947, GB-A-673 651).

The object of the present invention is therefore to develop a simple and economical process for the preparation of poly-p-xylylene and related derivatives.

This object is achieved according to the invention by a process in which readily accessible monomers are pyrolyzed in one stage to form the polymer.

The present invention accordingly relates to a process for preparing compounds of the formula (I)

$$\text{---}(CH_2\text{---}Ar\text{---}CH_2)_n\text{---} \qquad (I)$$

For this purpose compounds of the formula (II)

$$R\text{---}CO\text{---}O\text{---}CH_2\text{---}Ar\text{---}CH_2\text{---}O\text{---}CO\text{---}R \qquad (II)$$

are pyrolyzed in one stage under conditions resulting in cleavage of the ester bonds under a partial pressure of the esters of $p \leq 10$ mbar at temperatures $T \geq 500°$ C. with the formation of the corresponding quinodimethane derivatives, but without the latter, being cleaved further in subsequent reactions, followed by cooling and spontaneous polymerization with condensation of the quinodimethane derivatives, where Ar, R and n have the following meaning:

—Ar— is a 1,4-phenylene radical or another $C_6$–$C_{12}$ aromatic or heteroaromatic radical in which the bonds are in the para position or a comparable coaxial or antiparallel position and which is unsubstituted or substituted by one or more branched or unbranched, unsubstituted or halosubstituted $C_1$–$C_4$-alkyl, alkenyl or alkoxy radicals or $C_6$–$C_{12}$-aryl or heteroaryl radicals, hydroxyl, nitro, nitrile or amino groups or with R*—S— or R*—CO—O radicals, where R* is a $C_1$–$C_4$-alkyl radical or a $C_6$–$C_{12}$-aryl radical;

R— is a branched or unbranched $C_1$–$C_4$-alkyl or $C_6$–$C_{12}$-aryl radical or an R*—CO—O— radical, where R* has the meaning given above, and n is the degree of polymerization and is $\geq 2$.

The starting substances used according to the invention are compounds of the formula $$HOCH_2\text{---}Ar\text{---}CH_2OH.$$

The xylylenediols are reacted with carboxylic acid chlorides R—COCl by known methods of organic chemistry to form the xylylene diesters R—CO—OCH$_2$—Ar—CH$_2$O—CO—R, where R is a lower $C_1$–$C_4$-alkyl radical in the case of a monofunctional acid chloride, but may also be a further acid chloride functional group —COCl. Suitable monofunctional or difunctional reactants are acetyl chloride and oxalyl dichloride. Where bifunctional acid derivatives are used for the acetylation of the xylylenediols, the resultant ester chlorides Cl—C$_2$OC$_3$—CH$_2$—Ar—CH$_2$—C$_2$O$_3$—Cl are reacted with alcohols R*—OH to form the esters R*—C$_2$O$_4$—CH$_2$—Ar—CH$_2$—C$_2$O$_4$—R*, where R* is a branched or unbranched $C_1$–$C_4$ alkyl radical or a $C_6$–$C_{12}$- aryl radical.

According to the invention the esters thus obtained are subjected to pyrolysis under reduced pressure at temperatures of from 500° C. to 1000° C., preferably from 700° to 900° C. The reaction pressures are $p \leq 10$ mbar, preferably $p \leq 1$ mbar.

The residence times in the pyrolysis zone are chosen so that the esters are decomposed as far as possible to the corresponding quinodimethanes, but without the latter being thermally cleaved further in consecutive reactions. The gaseous quinodimethanes are cooled and condensed on a thermostatically controlled surface, where they spontaneously polymerize. The temperature of the condensation surface is below a critical condensation/polymerization temperature, above which no condensation and polymerization of the quinodimethanes occurs. This temperature is 30° C. for the preparation of unsubstituted poly-p-xylylene, and higher, but not above 130° C., for substituted poly-p-xylylenes. At the temperature prevailing in the condensation zone the saturation vapor pressure of the quinodimethanes is less than the pressure of the system.

Poly-p-xylylene is obtained as a thin, colorless film on the condensation surface. It is soluble in boiling chloronaphthalene or benzyl benzoate, from which it reprecipitates on cooling. The unsubstituted poly-p-xylylene prepared according to the invention softens at temperatures of $T \geq 300°$ C., and consequently corresponds to the specifications given in U.S. Pat. No. 3,342,754 for linear, uncrosslinked poly-p-xylylene, in contrast to the products formed from the one-stage high-temperature pyrolysis of p-xylene (GB-A-650 947, GB-A-673 651).

A particular advantage of the process according to the invention is that substituents on the aromatic ring can be introduced very easily and in a well-defined manner. For example, the substituted xylylenediols that are commercially available or that can easily be obtained by known organic chemistry reactions can be used to prepare substituted xylylene diesters, or alternatively the substituents on the aromatic ring can be introduced by similar reactions involving the xylylene diesters. The pyrolysis can then be carried out in an entirely analogous manner to the pyrolysis of the unsubstituted xylylene diesters.

According to the prior art, by contrast, substituents are introduced at the paracyclophane stage, isomer mixtures that are difficult to separate being obtained. According to this method the substituted homopolymers are obtained by fractional condensation, in which the differently substituted quinodimethane derivatives are condensed and polymerized at different temperatures. According to the prior art, by contrast, random copolymers of the differently substituted quinodimethanes are obtained by non-fractional condensation at room temperature (U.S. Pat. No. 3,288,728).

The process described here likewise enables random copolymers to be obtained in a very simple way. For this purpose a well-defined mixture of two or more differently substituted xylylene diesters is used in the pyrolysis stage and the components of the mixture are pyrolyzed jointly under identical conditions. The mixture of the resultant substituted quinodimethanes is condensed out jointly at a temperature below the critical condensation temperature of the most readily volatile derivative and yields a random copolymer.

EXAMPLES

Example 1

Preparation of 1,4-bis(isopropoxyoxalatomethyl)benzene 32 ml of 1,4-bis(hydroxymethyl)benzene were dissolved in 150 ml of toluene and 50 ml of THF with exclusion of air and moisture. 10 g of oxalyl dichloride were then dissolved in 150 ml of anhydrous THF at 0° C. and 50 ml of anhydrous toluene were added dropwise, the mixture was stirred, first of all at room temperature and then under reflux, and finally the solvents and excess acid chloride were distilled off under reduced pressure. The 1,4-bis(chlorooxalatomethyl)benzene remaining as solid residue in 88% of the theoretical yield were dried under reduced pressure. 4.54 g of the substance were dissolved in toluene with exclusion of air and moisture. By adding this solution dropwise to 500 ml of isopropanol, 1,4-bis(isopropoxyoxalatomethyl)-benzene $C_6H_4(CH_2C_2O_4C_3H_7)_2$ was obtained as a colorless precipitate in 65% yield.

Example 2

Preparation of 1,4-bis(acetatomethyl)benzene 10.95 g of 1,4-bis(hydroxymethyl)benzene were placed in a flask with exclusion of air and moisture, and 50 ml of acetyl chloride were added dropwise. The reaction mixture was stirred at room temperature and the excess acetyl chloride was distilled off. 1,4-Bis-(acetatomethyl)benzene was obtained as a pale yellow residue in 94% of the theoretical yield.

Example 3

Pyrolysis of the Esters 1 mmol of the compounds prepared according to Examples 1 and 2 was introduced into a small quartz boat and placed in a quartz tube at the beginning of the pyrolysis zone in a preheated furnace (Heraeus Tubular Furnace RO 4/25 with regulating device RE 1.1). After the evacuation of the quartz tube the substance vaporized, flowed through the pyrolysis zone, where it decomposed, and finally precipitated as a film on the condensation surface behind the furnace. Poly-p-xylylene was obtained at pyrolysis temperatures above 600° C. The best yields were obtained at temperatures of from 700° to 900° C.

The elementary analyses of all polymerization products agreed, within the limits of experimental error, with the calculated values for the empirical formula $C_8H_8$. The IR spectra of the films corresponded to those for poly-p-xylylene given in the literature (Encyclopedia of Polym. Sci. Techn. 15, 98, New York 1971).

Example 4

Preparation of 1,4-bis(pivalatomethyl)-2-chlorobenzene 3 g of 1,4-bis(hydroxymethyl)-2-chlorobenzene were placed in a flask with exclusion of air and moisture and 20 ml of pivalyl chloride were added dropwise. The reaction mixture was stirred at room temperature and the excess pivalyl chloride was distilled off. 1,4-bis(-Pivalatomethyl)-2-chlorobenzene was obtained as a pale yellow liquid in 93% of the theoretical yield.

Example 5

Pyrolysis of 1,4-bis(pivalatomethyl)-2-chlorobenzene 1 mmol of 1,4-bis(pivalatomethyl)-2-chlorobenzene was introduced into a small quartz boat and placed in a quartz tube at the beginning of the pyrolysis zone in a preheated furnace (Hereaus Tubular Furnace (RO 4/25 with regulating device RE 1.1). After the evacuation of the quartz tube the substance vaporized, flowed through the pyrolysis zone, where it decomposed, and finally precipitated as a film on the condensation surface behind the furnace. Poly-p-chloroxylylene was obtained at pyrolysis temperatures above 700° C. The best yields were obtained at temperatures of from 800°–900° C.

We claim:

1. A process for preparing polymers of p-xylylene having repeating units of the formula (I)

   (I)

by pyrolysis, where n is the degree of polymerization and is $\geq 2$, wherein ester compounds of the formula (II)

$$-R-CO-O-CH_2-Ar-CH_2-O-CO-R \qquad (II)$$

are pyrolyzed in one stage under conditions resulting in cleavage of the ester bonds under a partial pressure of the esters of $p \leq 10$ mbar at temperatures $T \geq 500°$ C., with the formation of corresponding derivatives of 1,4-dimethylene-2,5-cyclohexadiene, but without the latter being cleaved further in subsequent reactions, and the polymers of p-xylylene formed by spontaneous polycondensation of the derivatives of 1,4-dimethylene-2,5-cyclohexadiene were then cooled, Ar and R have the following meanings:

—Ar— is a 1,4-phenylene radical or another $C_6$-$C_{12}$ aromatic or heteroaromatic radical in which the bonds are in the para position or a comparable coaxial or antiparallel position and which is unsubstituted or substituted by one or more branched or unbranched, unsubstituted or halosubstituted $C_1$-$C_4$-alkyl, alkenyl or alkoxy radicals or $C_6$-$C_{12}$-aryl or heteroaryl radicals, hydroxyl, nitro, nitrile or amino groups or with $R^*$—S— or $R^*$—CO—O radicals, where $R^*$ is a $C_1$-$C_4$-alkyl radical or a $C_6$-$C_{12}$-aryl radical;

R— is branched or unbranched $C_1$-$C_4$-alkyl or $C_6$-$C_{12}$-aryl radical or an $R^*$—CO—O radical, where $R^*$ has the meaning given above.

2. The process as claimed in claim 1, wherein the pyrolysis temperature is in the range from 500° to 1000° C.

3. The process as claimed in claim 1, wherein the pyrolysis of the compounds of the formula (II) and the condensation of the derivatives of 1,4-dimethylene-2,5-cyclohexadiene formed therefrom is at a partial pressure $p \leq 10$ mbar.

4. The process as claimed in claim 1, wherein two or more differently substituted xylylene diesters are pyrolyzed.

5. The process as claimed in claim 1, wherein the pyrolysis temperature is in the range from 700° to 900° C.

6. The process as claimed in claim 1, wherein the pyrolysis of the compounds of the formula (II) and the condensation of the derivatives of 1,4-dimethylene-2,5-cyclohexadiene formed therefrom is at a partial pressure $p \leq 1$ mbar.

7. A process for preparing polymers of p-xylylene having repeating units of the formula (I)

$$+CH_2-Ar-CH_2)_{\overline{n}} \qquad (I)$$

by pyrolysis, where n is the degree of polymerization and is $\geq 2$, wherein ester compounds of the formula (II)

$$-R-CO-O-CH_2-Ar-CH_2-O-CO-R \qquad (II)$$

are pyrolyzed in on stage under conditions resulting in cleavage of the ester bonds under a partial pressure of the esters of $p \leq 10$ mbar at temperatures $T \geq 500°$ C., with the formation of corresponding derivatives of 1,4-dimethylene-2,5-cyclohexadiene and the polymers of p-xylylene formed by spontaneous polycondensation of the derivatives of 1,4-dimethylene-2,5-cyclohexadine, then cooled, where Ar and R have the following meanings:

—Ar— is a 1,4-phenylene radical or another $C_6$-$C_{12}$ aromatic or heteroaromatic radical in which the bonds are in the para position or a comparable coaxial or antiparallel position and which is unsubstituted or substituted by one or more branched or unbranched, unsubstituted or halosubstituted $C_1$-$C_4$-alkyl, alkenyl or alkoxy radicals or $C_6$-$C_{12}$-aryl or heteroaryl radicals, hydroxyl, nitro, nitrile or amino groups or with $R^*$—S— or $R^*$—CO—O radicals, where $R^*$ is a $C_1$-$C_4$-alkyl radical or a $C_6$-$C_{12}$-aryl radical;

R— is branched or unbranched $C_1$-$C_4$-alkyl or $C_6$-$C_{12}$-aryl radical or an $R^*$—CO—O radical, where $R^*$ has the meaning given above.

* * * * *

UNITED STATES PATENT AND TRADEMARK OFFICE
CERTIFICATE OF CORRECTION

PATENT NO. : 5,310,858
DATED : May 10, 1994
INVENTOR(S) : Greiner et al.

It is certified that error appears in the above-identified patent and that said Letters Patent is hereby corrected as shown below:

In column 1, line 45, after the word "paracyclophane", insert --EP-A-294 651-- instead of "EP-A-294 851".

Signed and Sealed this

Nineteenth Day of September, 1995

Attest:

BRUCE LEHMAN

Attesting Officer

Commissioner of Patents and Trademarks